US010027157B2

United States Patent
Labbe et al.

(10) Patent No.: US 10,027,157 B2
(45) Date of Patent: *Jul. 17, 2018

(54) IMPLANT CURRENT CONTROLLED BATTERY CHARGING BASED ON TEMPERATURE

(71) Applicant: Nuvectra Corporation, Plano, TX (US)

(72) Inventors: Michael Labbe, Twinsburg, OH (US); Les Halberg, Valencia, CA (US); Benjamin Cottrill, Cleveland, OH (US)

(73) Assignee: Nuvectra Corporation, Plano, TX (US)

( * ) Notice: Subject to any disclaimer, the term of this patent is extended or adjusted under 35 U.S.C. 154(b) by 32 days.

This patent is subject to a terminal disclaimer.

(21) Appl. No.: 14/977,768

(22) Filed: Dec. 22, 2015

(65) Prior Publication Data
US 2016/0118842 A1    Apr. 28, 2016

Related U.S. Application Data

(63) Continuation of application No. 13/607,037, filed on Sep. 7, 2012, now Pat. No. 9,225,190.

(51) Int. Cl.
*H02J 7/04* (2006.01)
*H02J 7/16* (2006.01)
(Continued)

(52) U.S. Cl.
CPC .............. *H02J 7/025* (2013.01); *A61N 1/378* (2013.01); *A61N 1/3787* (2013.01); *G01K 13/00* (2013.01);
(Continued)

(58) Field of Classification Search
CPC .......... H02J 7/025; H02J 50/10; H02J 7/0004; H02J 2007/0096; H02J 7/0029;
(Continued)

(56) References Cited

U.S. PATENT DOCUMENTS

| 359,907 A | 3/1887 | Thompson et al. |
| 3,911,350 A | 10/1975 | Swope |

(Continued)

FOREIGN PATENT DOCUMENTS

| GB | 724175 | 8/1950 |
| GB | 1316169 | 5/1973 |

(Continued)

*Primary Examiner* — Nghia Doan
(74) *Attorney, Agent, or Firm* — Haynes and Boone, LLP

(57) ABSTRACT

A method for wirelessly charging a battery in an implantable medical device including the steps of: providing a receiver in the implantable medical device and providing a temperature sensor in the implantable medical device. The method also includes receiving, via the receiver, a wireless power signal from an external charger and converting the wireless power signal into a battery charge signal including power for recharging the battery. The method yet also includes sensing a temperature of the implantable medical device with the temperature sensor. The method further includes changing a current of the battery charge signal from a first non-zero current to a second non-zero current that is different from the first non-zero current. Changing of the current of the battery charge signal is based on the temperature sensed by the temperature sensor.

25 Claims, 8 Drawing Sheets

(51) Int. Cl.
*H02J 7/06* (2006.01)
*H02J 7/02* (2016.01)
*A61N 1/378* (2006.01)
*H02J 7/00* (2006.01)
*G01K 13/00* (2006.01)

(52) U.S. Cl.
CPC .............. *H02J 7/007* (2013.01); *H02J 7/047* (2013.01); *H02J 2007/0096* (2013.01)

(58) Field of Classification Search
CPC .. H02J 7/047; H02J 50/20; H02J 50/12; H02J 50/90; H02J 7/0021; H02J 7/0091
USPC ............... 320/108, 143–144, 152–154, 150; 607/60–63, 102–103
See application file for complete search history.

(56) References Cited

U.S. PATENT DOCUMENTS

| | | | |
|---|---|---|---|
| 3,970,912 A | 7/1976 | Hoffman | |
| 4,045,720 A | 8/1977 | Alexandres | |
| 4,082,097 A | 4/1978 | Mann et al. | |
| 4,125,802 A | 11/1978 | Godard | |
| 4,441,498 A | 4/1984 | Nordling | |
| 4,623,597 A | 11/1986 | Sapru et al. | |
| 4,670,703 A | 6/1987 | Williams | |
| 5,279,292 A | 1/1994 | Baumann et al. | |
| 5,314,457 A | 5/1994 | Jeutter et al. | |
| 5,325,040 A | 6/1994 | Bogut et al. | |
| 5,411,537 A | 5/1995 | Munshi et al. | |
| 5,591,546 A | 1/1997 | Nagaura | |
| 5,713,939 A | 2/1998 | Nedungadi et al. | |
| 5,948,006 A | 9/1999 | Mann | |
| 6,118,250 A | 9/2000 | Hutchison, IV et al. | |
| 6,181,105 B1 | 1/2001 | Chutolo et al. | |
| 6,227,204 B1 | 5/2001 | Baumann et al. | |
| 6,245,464 B1 | 6/2001 | Spillman et al. | |
| 6,348,777 B1 | 2/2002 | Brown et al. | |
| 6,415,186 B1 | 7/2002 | Chim et al. | |
| 6,476,584 B2 | 11/2002 | Sakakibara | |
| 6,553,263 B1 | 4/2003 | Meadows et al. | |
| 6,772,011 B2 | 8/2004 | Dolgin | |
| 7,208,915 B2 | 4/2007 | Kubota et al. | |
| 7,505,816 B2 | 3/2009 | Schmeling et al. | |
| 7,711,419 B2 | 5/2010 | Armstrong et al. | |
| 7,805,200 B2 | 9/2010 | Kast et al. | |
| 7,818,068 B2 | 10/2010 | Meadows et al. | |
| 7,865,245 B2 | 1/2011 | Torgerson et al. | |
| 7,962,222 B2 | 6/2011 | He et al. | |
| RE42,682 E | 9/2011 | Barreras, Sr. et al. | |
| 8,170,681 B2 | 5/2012 | Jimenez et al. | |
| 8,260,432 B2 | 9/2012 | DiGiore et al. | |
| 8,401,663 B2 | 3/2013 | Aghassian | |
| 8,401,664 B2 | 3/2013 | Chow et al. | |
| 8,428,712 B2 | 4/2013 | Davis et al. | |
| 8,463,392 B2 | 6/2013 | Aghassian | |
| 8,473,066 B2 | 6/2013 | Aghassian et al. | |
| 8,594,804 B2 | 11/2013 | Joshi | |
| 2004/0039423 A1 | 2/2004 | Dolgin | |
| 2006/0247738 A1 | 11/2006 | Schmeling et al. | |
| 2008/0027500 A1 | 1/2008 | Chen | |
| 2009/0149917 A1 | 6/2009 | Whitehurst et al. | |
| 2009/0326611 A1 | 12/2009 | Gillbe | |
| 2010/0010582 A1* | 1/2010 | Carbunaru | H01M 10/443 607/61 |
| 2010/0025671 A1 | 2/2010 | Dinsmoor et al. | |
| 2010/0256709 A1 | 10/2010 | Kallmyer | |
| 2010/0277128 A1 | 11/2010 | Tam et al. | |
| 2010/0305662 A1 | 12/2010 | Ozawa et al. | |
| 2011/0071597 A1* | 3/2011 | Aghassian | A61N 1/37235 607/61 |
| 2011/0127970 A1 | 6/2011 | Wang et al. | |
| 2011/0181241 A1 | 7/2011 | Badger | |
| 2011/0190853 A1 | 8/2011 | Dinsmoor et al. | |
| 2012/0074893 A1 | 3/2012 | Cole | |
| 2012/0119699 A1 | 5/2012 | Carbunaru et al. | |
| 2012/0161945 A1 | 6/2012 | Single et al. | |
| 2012/0191151 A1 | 7/2012 | Kameli | |
| 2012/0223590 A1* | 9/2012 | Low | H02J 5/005 307/104 |
| 2012/0239118 A1 | 9/2012 | Ozawa et al. | |
| 2012/0277831 A1 | 11/2012 | Joshi | |
| 2013/0096653 A1 | 4/2013 | Winstrom | |
| 2013/0165993 A1 | 6/2013 | Aghassian et al. | |
| 2013/0193912 A1 | 8/2013 | Bornhoft | |
| 2013/0193928 A1* | 8/2013 | Prosser | H02J 7/0042 320/130 |

FOREIGN PATENT DOCUMENTS

| | | |
|---|---|---|
| JP | 1006384 A | 1/1989 |
| JP | 1014881 A | 1/1989 |
| JP | 64002258 A | 1/1989 |
| JP | 3192663 A | 8/1991 |
| JP | 6203829 A | 7/1994 |
| JP | 6349493 A | 12/1994 |
| JP | 8185851 A | 7/1996 |
| WO | 2004002572 A1 | 1/2004 |
| WO | 2010059097 A1 | 5/2010 |

\* cited by examiner

IMPLANT CURRENT CONTROLLED BATTERY CHARGING BASED ON TEMPERATURE

CROSS-REFERENCES TO RELATED APPLICATIONS

This application is a continuation of U.S. patent application Ser. No. 13/607,037 filed on Sep. 7, 2012, and incorporated herein by reference. This application is related to U.S. Pat. No. 9,209,634 issued on Dec. 8, 2015, and incorporated herein by reference. This application is also related to U.S. Pat. No. 9,142,989 issued on Sep. 22, 2015, and incorporated herein by reference. This application is also related to U.S. patent application Ser. No. 14/942,243 filed on Nov. 16, 2015, and incorporated herein by reference.

BACKGROUND

This application relates generally to rechargeable medical devices, and this application relates more specifically to electrically powered implantable medical devices (IMDs) that include rechargeable batteries that are charged through the skin using inductive charging techniques.

The electrical circuits of IMDs are used to monitor the patient, disperse medications, and also to apply therapeutic electrical stimulation to tissue. Electrically driven implantable devices are used, for example, as neuro-stimulators including pain suppression, hearing aids (e.g. cochlear devices), cardiac pacemakers, and defibrillators. However, IMDs may also be used for drug infusion and dispensing systems, nerve and bone growth stimulators, digestive track stimulators, artificial vision apparatus, artificial organs including artificial hearts, bladder stimulators, and for the purposes of implanted sensors that monitor but do not actively stimulate tissue. Additionally, IMDs have been used as combinations of the above listed devices, such as a combined cardiac pacemaker and cardiac defibrillator. Thus, the electrical circuitry can provide therapeutic electrical stimulation of tissue, monitor the patient, and dispense medication.

These IMDs often have power requirements in excess of what can be provided by conventional batteries (without cumbersome replacement processes), thus rechargeable batteries are often provided in the implanted device. This prevents the need for electrical wiring that protrudes from a patient's skin, which presents an infection hazard. Therefore, implant rechargeable batteries are often charged via an inductive signal provided by an external charger to a charge receiving coil of the implant. This enables recharging of the battery through the patient's skin without physical contact between the implant and the external charging unit.

However, the traditional inductive recharging process for IMDs requires that a user sit relatively still during the recharging period to maintain alignment between the IMD and an external charging unit which provides the inductive signal that is converted into electricity for charging the IMD internal battery. This can interfere with the user's lifestyle.

Additionally, newer implants that include neuro-stimulators, often consume relatively large amounts of power in comparison to older pacemakers which provide low power electrical stimulation signals. These newer implants require more frequent charging, with some requiring a recharging interval of two weeks or less, and thus patients expend a considerable amount of time charging their IMDs.

In the past, charging times for the rechargeable batteries for IMDs were limited by a number of factors including battery chemistries. However, with the introduction of newer lithium ion batteries and other batteries, battery chemistry is no longer the primary limitation to recharging of IMDs. Instead, temperature limitations inside the human body that result from the recharging process of the implant are becoming an increasingly problematic limitation that prevents faster battery charging.

During charging, some of the inductively transferred energy provided to the IMD is converted into heat as opposed to being converted into electricity for recharging. Eddy currents form in the housing of the IMD during charging and these currents are converted into undesirable heat. Also, some of the inductive signal in the recharging circuitry within the IMD is also converted into heat. As a result, this waste heat will raise the temperature of the IMDs, potentially to undesirable levels if not properly monitored. Conventional approaches for controlling temperature during inductive charging typically included completely shutting down charging if an excessive temperature level is reached, or charging the implant's battery at relatively low charging rates to avoid exceeding temperature limitations. However, shutting down the charging process is inefficient and can increase charging times and reduce charging efficiencies. Charging at lower charging rates also increases the charging times for IMDs.

Desired is a way to overcome one or more of the shortcomings of the prior art described above.

SUMMARY

Provided are a plurality of example embodiments, including, but not limited to, a method for wirelessly charging a battery in an implantable medical device including the steps of: providing a receiver in the implantable medical device and providing a temperature sensor in the implantable medical device. The method also includes receiving, via the receiver, a wireless power signal from an external charger and converting the wireless power signal into a battery charge signal including power for recharging the battery. The method yet also includes sensing a temperature of the implantable medical device with the temperature sensor. The method further includes changing a current of the battery charge signal from a first non-zero current to a second non-zero current that is different from the first non-zero current. Changing of the current of the battery charge signal is based on the temperature sensed by the temperature sensor.

Also provided is a method for wirelessly charging a battery in an implantable medical device, the method comprising the steps of: providing a receiver in the implantable medical device and also providing a temperature sensor in the implantable medical device. The method also including receiving, via the receiver, a wireless power signal from an external charger and converting the wireless power signal into a battery charge signal including power for recharging the battery. The method yet also includes sensing temperature information of the implantable medical device with the temperature sensor. The method further includes controlling a current of the battery charge signal based on the temperature information sensed by the temperature sensor, such that when the temperature is less than a low temperature threshold the battery charge signal is provided at a first non-zero current, and when the temperature is greater than a high temperature threshold the battery charge signal is provided at a second non-zero current that is less than the first non-zero current.

Still further provided is a method for wirelessly charging a battery in an implantable medical device, the method including the steps of: providing a receiver in the implantable medical device and also providing a temperature sensor in the implantable medical device. The method also includes receiving, via the receiver, a wireless power signal from an external charger and converting the wireless power signal into a battery charge signal including power for recharging the battery. The method yet also includes sensing temperature information of the implantable medical device with the temperature sensor and obtaining historical temperature information based on the temperature information sensed by the temperature sensor over a period of time. The method further includes using a charge controller for selecting a current of the battery charge signal, using a control algorithm, based on the temperature information and historical temperature information, such that, the temperature is prevented from exceeding a charging temperature threshold.

Also provided is a method for wirelessly charging a battery in an implantable medical device, the method including the steps of: providing a receiver in the implantable medical device and providing a temperature sensor in the implantable medical device. The method also including receiving, via the receiver, a wireless power signal from an external charger and converting the wireless power signal into a battery charge signal including power for recharging the battery. The method further including sensing a temperature of the implantable medical device with the temperature sensor and controlling a current of the battery charge signal to maintain the temperature at a target temperature.

Still further provided is a method of providing a neurostimulation therapy to a patient, including the steps of: providing an implantable medical device having a battery that recharging and being implanted in a patient, using said implantable medical device for driving at least one electrode implanted in the patient to stimulate at least one nerve of the patient, and wirelessly charging the battery in the implantable medical device. The steps of wirelessly charging include the steps of: providing a receiver in the implantable medical device and providing a temperature sensor in the implantable medical device. The steps of wirelessly charging include receiving, via the receiver, a wireless power signal from an external charger, converting the wireless power signal into a battery charge signal including power for recharging the battery, and sensing a temperature of the implantable medical device with the temperature sensor. The steps of wirelessly charging further include changing a current of the battery charge signal from a first non-zero current to a second non-zero current that is different from the first non-zero current, wherein said changing of the current of the battery charge signal is based on the temperature sensed by the temperature sensor.

Also provided are additional example embodiments, some, but not all of which, are described herein below in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which.

DETAILED DESCRIPTION OF THE EXAMPLE EMBODIMENTS

Figure 1:
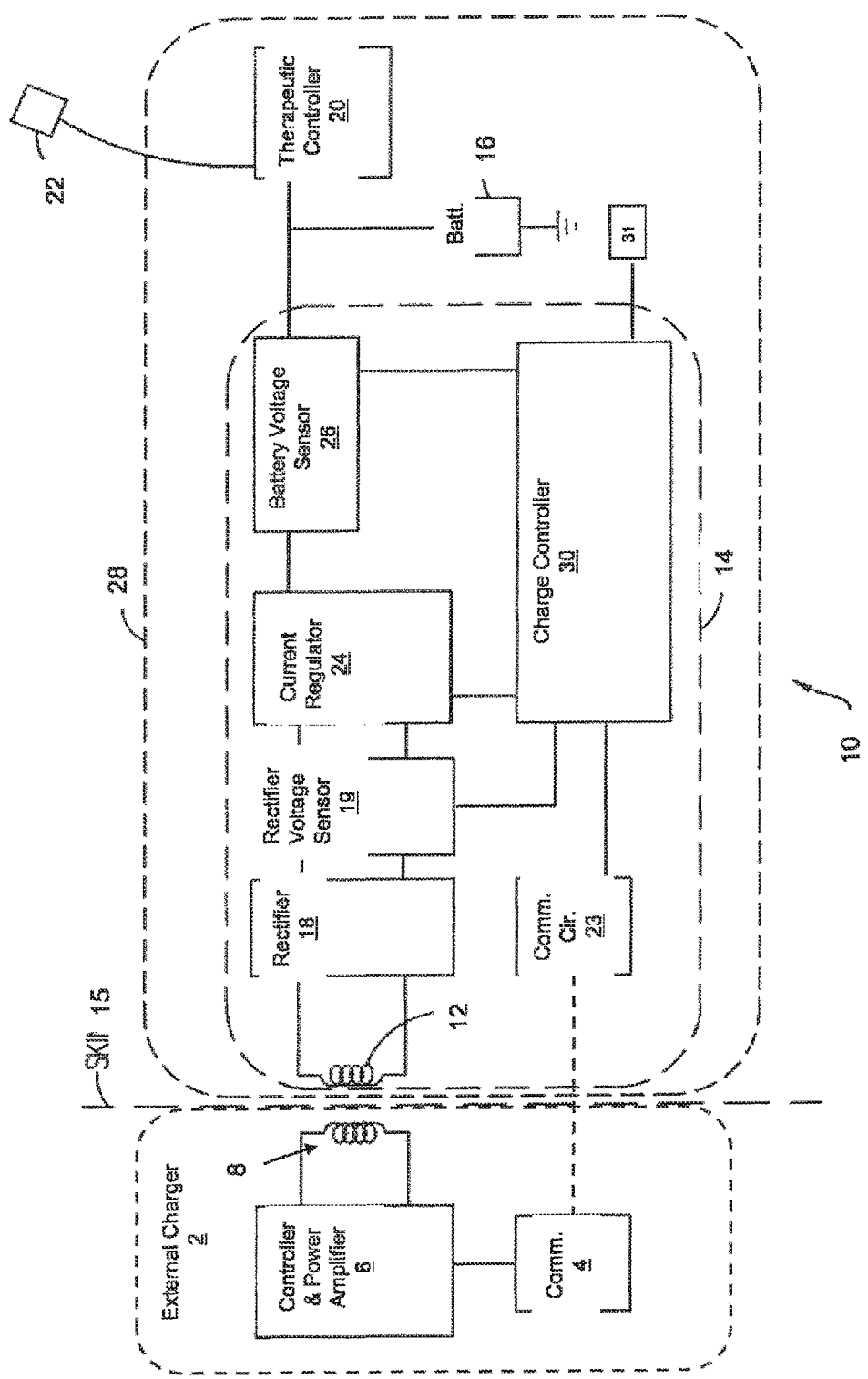
FIG. 1 shows example embodiment of an external charger and an implantable medical device that are wirelessly linked during a power transfer for charging a battery.

FIG. 1 shows an example embodiment of an external charger 2 and an IMD 10 that are wirelessly or inductively (i.e. electromagnetically) linked where the external charger 2 provides power to the IMD 10. The inductive signal is sent to the IMD 10 and is received by the receiving coil 12 of the recharging circuitry 14 through the patient's skin 15. The recharging circuitry 14 recharges the battery 16 which may be a lithium ion rechargeable battery. The external charger also includes a communication circuitry 4 that communicates with the IMD 10.

The primary coil of the external charger can be driven at a resonant frequency ranging from a few KHz to several MHz with the secondary receiving coil 12 tuned to the same frequency. The induced AC voltage on the implant is converted to a DC voltage by the rectifier 18. The current regulator 24 converts the DC output from the rectifier 18 into a controlled current or a controlled voltage signal for recharging the battery 16.

The recharging circuitry 14 also includes a battery voltage sensor 26 that periodically monitors the voltage of the rechargeable battery 16. The charge controller 30 uses the voltage measured by the voltage sensor 26 to control the current regulator 24 to provide a particular current or voltage source for charging. The charge controller 30 can control the voltage and/or current of the DC power and provide the controlled current or voltage to the battery for recharging. The current regulator 24 may include battery protection circuitry.

A rectifier voltage sensor 19 senses the voltage of the rectifier 18, and that voltage measurement may be transmitted by communication circuitry 23 to the communication circuitry 8 of external charger 2. The external charger 2 then may adjust the strength, frequency, or other characteristics of the inductive power signal based on the voltage of the rectifier 18. The IMD 10 also includes a temperature sensor 31 that detects the temperature within the implant and/or on the implant housing 28. In some embodiments, the temperature sensor 31 may consist of two or more temperature sensors located at different locations within the implant. The charger controller 30 uses the temperature from the temperature sensor as a basis for adjusting the charging power to the battery 16. The communication circuitry 23 may optionally transmit the temperature of the IMD 10, sensed by a temperature sensor 31, to the communication circuitry 8 of the external charger 2. The IMD 10 also includes a therapeutic controller 20 for providing a therapeutic electrical signal to a patient using a therapeutic lead 22.

Figure 2:
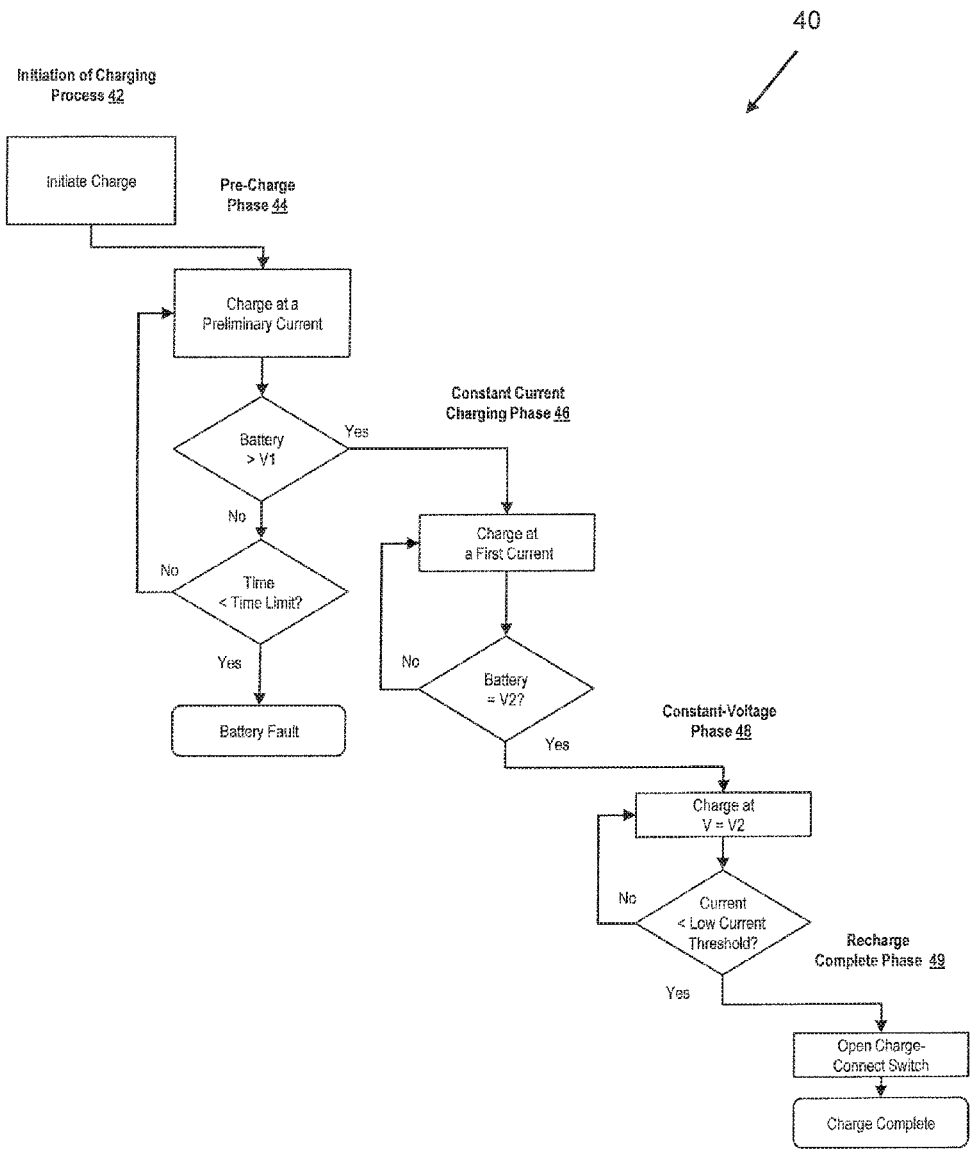
FIG. 2 is an example flow chart showing a current controlled charging methodology, with an optional voltage controlled charging phase, that uses charging parameters that are voltage based.

FIG. 2 shows an example flow chart showing a current controlled charging methodology 40, with an optional voltage controlled charging phase that uses charging parameters that are voltage based. The charging methodology 40 includes initiation of the charging process 42 and entry of the pre-charge phase 44. The pre-charge phase 44 is maintained as long as the battery voltage is below a low voltage threshold V1 for less than a time limit. If pre-charge phase 44 exceeds the time limit, a battery fault is detected and charging is stopped. During the pre-charge phase 44 the rechargeable battery is charged at a preliminary charge current. The charge rate of the battery is generally expressed as a function of rated capacity C of the battery, typically in mAh, or the C-rate. The current being supplied for charging can be denoted as C/n. For example, a battery that is discharged will take two hours to charge if charged at a rate (e.g. current) of C/2. The same discharged battery will take four hours to charge if charged at a rate of C/4. Thus, the time to charge a battery is inversely proportional to the C-rate of the battery.

The charging methodology 40 also includes a current controlled charge phase 46 during which the rechargeable battery is charged at a first charge current that is a higher current than the current of the preliminary charge current. It is during the current controlled charge phase 46 that heating of the IMD would likely become an issue because larger charging currents correspond to larger inductive power levels (e.g. larger inductive fields) from the external charger. A large inductive signal generates eddy currents in the implant's housing which cause heating of the implant. Also, the recharging circuitry dissipates a portion of the inductive signal as heat. In cases where excess temperature is detected in the implant, charging is simply stopped until the temperature decreases to a safe level. Switching between full charge rate and zero charge rate is inefficient and adds to the overall charging time of the device, and thus is to be avoided.

The charging methodology 40 optionally includes a constant-voltage phase 48 that tops off the rechargeable battery by providing a constant voltage when the battery voltage equals or is greater than V2, a voltage greater than V1. During the constant-voltage phase 48 the charger monitors the current supplied to the battery and stops charging when the current drops below a low current threshold, which indicates that the battery is fully charged and prevents damage to the battery from occurring due to overcharging. After the current drops below the low current threshold during the constant-voltage phase 48, the charging methodology enters a recharge complete 49 phase and stops charging.

Figure 3:
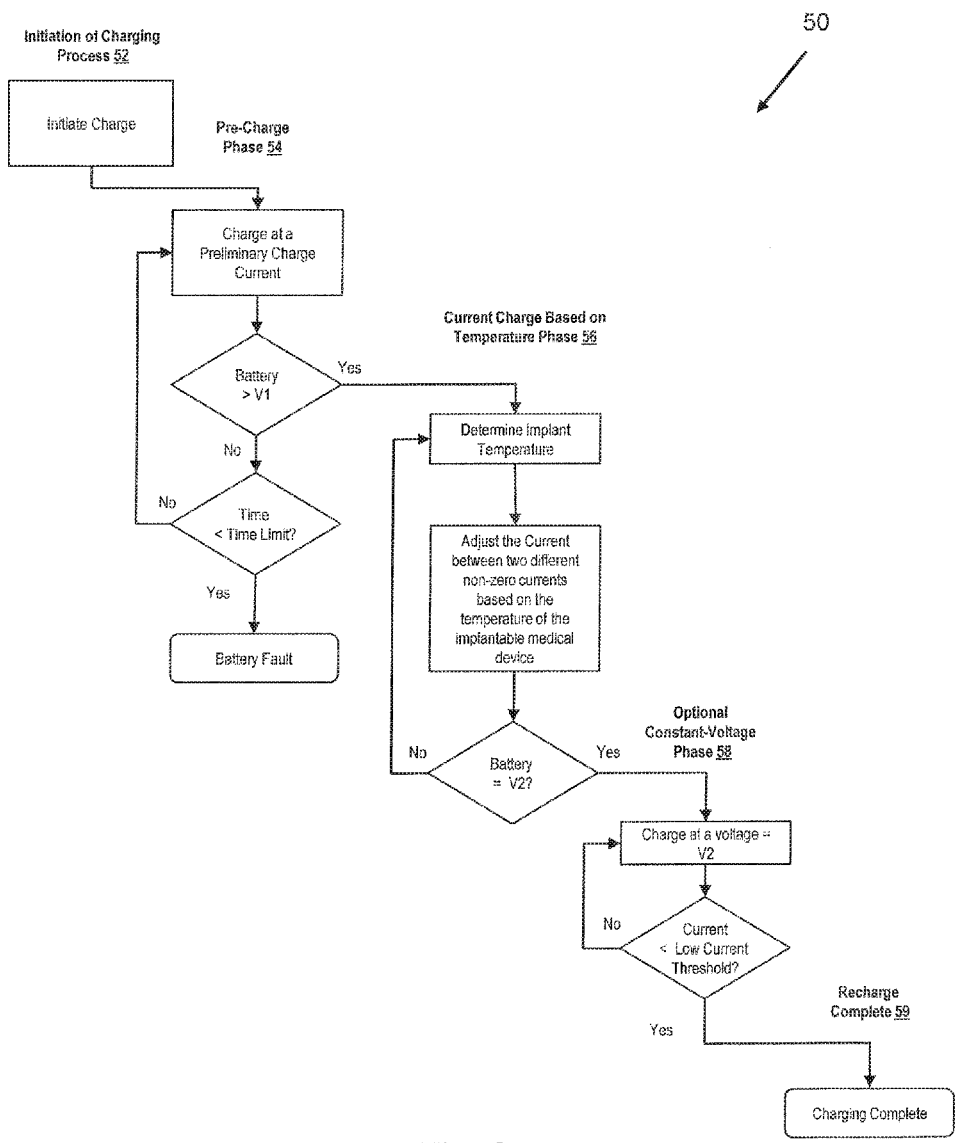
FIG. 3 is an example flow chart of a current controlled charging methodology, with an optional voltage controlled charging phase, that uses charging parameters that include both voltage and temperature as the basis for controlling the charge.

FIG. 3 is an example flow chart of a current controlled charging methodology 50, with an optional voltage controlled charging phase, that uses charging parameters that include both voltage and temperature as the basis for controlling the charge. It is understood that the voltage parameter is optional in the charging methodologies of the application and is given for purpose of example. The charging methodology 50 includes initiation of the charging process 52. Next, a pre-charge phase 54 provides a preliminary charge current to the battery when the battery is below a voltage of V1. Additionally, the pre-charge phase 54 may be time limited to indicate a battery fault if the battery voltage does not exceed V1 within a time limit. After the pre-charging process 52 completes, methodology 50 then enters a current charge based on temperature phase 56 that uses the temperature of the implant as a basis for adjusting the current for recharging the battery between two different non-zero charge currents (e.g. a first non-zero current, a second non-zero current) to prevent excessive heating while the battery voltage is below a voltage V2, which is greater than V1. For example, the current supplied to the battery could be approximately C/4, or optionally an even higher current up to or above C/2. The current for charging the battery may start at a relatively high current but then be decreased in response to temperature readings from the temperature sensor of the IMD.

Once the battery voltage equals V2 the charging methodology 50 then enters into an optional constant-voltage phase 58 that provides a constant voltage (e.g. constant voltage equal to V2) to the battery until the battery accepts less current than a low current threshold. For example, once the current to the battery drops below C/20 during the optional constant voltage phase 58, that phase ends and the methodology enters the recharge complete phase 59.

Figure 4:
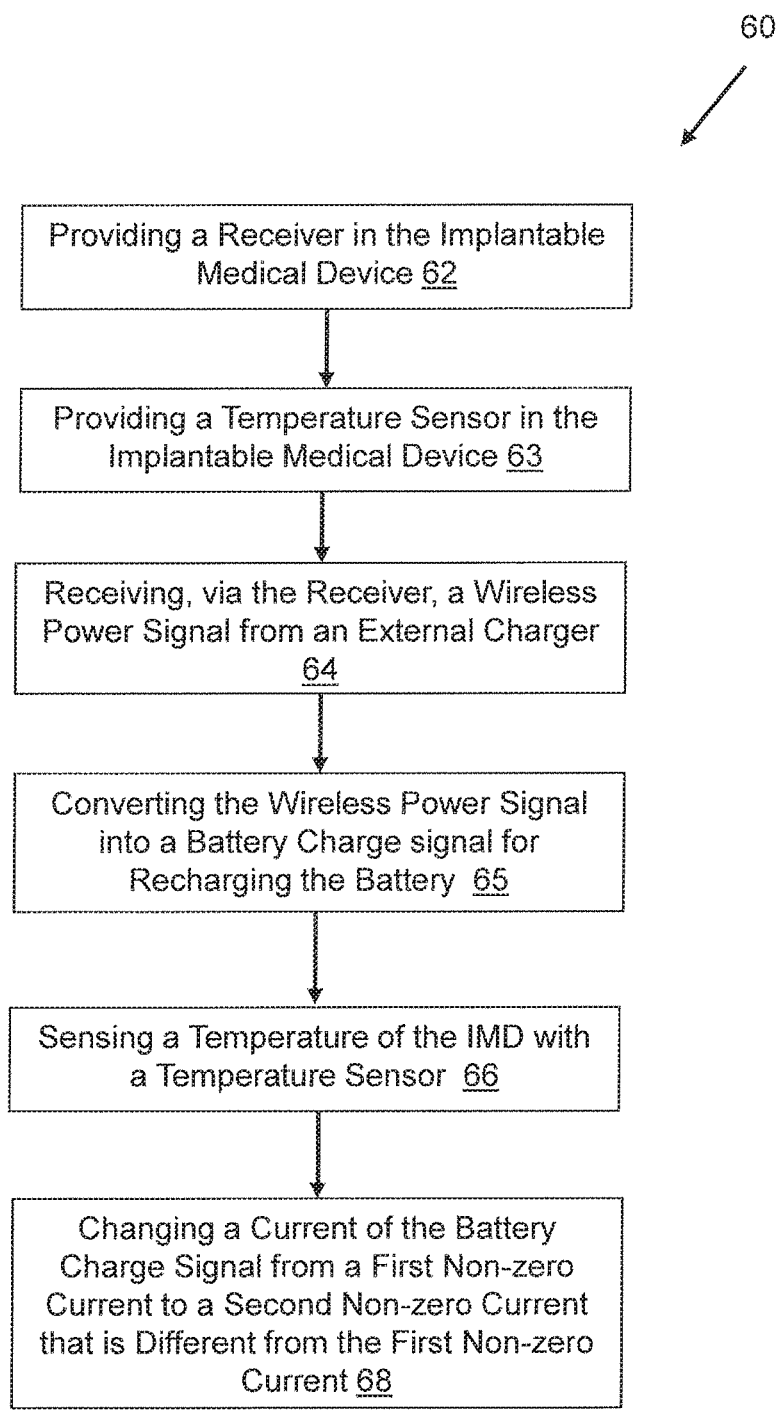
FIG. 4 is an example current controlled charging method for controlling a current of a rechargeable battery in an IMD that uses charging parameters including both voltage and temperature as basis for controlling the charge.

FIG. 4 shows an example method 60 for wirelessly charging a battery in an implantable medical device. The method 60 controls a current for recharging a battery in an IMD and uses temperature as a basis for controlling the current of the recharge and optionally may use other parameters including battery voltage, recharging circuitry voltage, and the battery's ability to accept current. The method 60 may correspond to the constant current charging phase 46 of FIG. 2. The temperature can include the temperature of the IMD, a rate of change of the temperature of the IMD, and/or a series of temperature readings from the IMD taken over time to reflect historical temperature information. The temperature of the IMD may be taken from a single temperature sensor or from multiple temperature sensors.

The charging method 60 includes the steps of providing a receiver in the implantable medical device 62. The receiver may be a receiver coil, antenna, or other receiving device for receiving a wireless power signal. The charging method 60 also includes providing a temperature sensor in the implantable medical device 63. The temperature sensor provides temperature information to the charge controller and/or other controllers of the IMD. The method 60 further includes receiving, via the receiver, a wireless power signal from an external charger 64. The wireless power signal may include an inductive power signal, an electromagnetic power signal, or other wireless signal that can be converted into power for recharging the battery. The wireless signal may or may not include information. The charging method 60 also includes converting the wireless power signal into a battery charge signal for recharging the battery 65. The charging method 60 further includes sensing a temperature of the IMD with a temperature sensor 66. The charge controller uses readings from the temperature sensor as a basis for adjusting and/or determining the current to provide to the rechargeable battery.

The charging method 60 still further includes changing a current of the battery charge signal from a first non-zero current to a second non-zero current that is different from the first non-zero current 68. The changing of the current of the battery charge signal is based on the temperature sensed by the temperature sensor. Changing the current of battery charge signal may include decreasing the current when the temperature sensed by said temperature sensor indicates an increased temperature in the implantable medical device and increasing the current when the temperature sensed by said temperature sensor indicates a decreased temperature in the implantable medical device.

Figure 5:
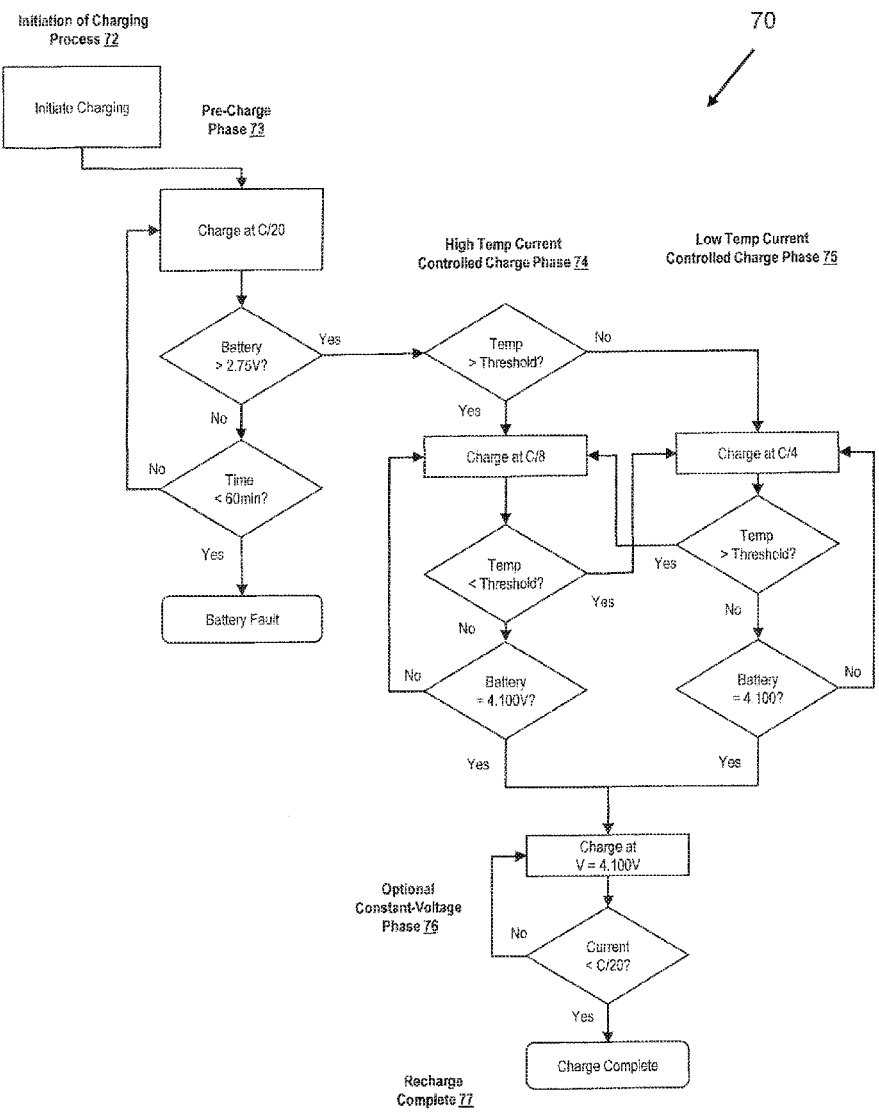
FIG. 5 is another example flow chart of a current controlled charging methodology that uses hysteresis control.

FIG. 5 is a an example flow chart of a current controlled charging methodology 70, with an optional voltage controlled charging phase 76, that uses charging parameters that include both voltage and temperature as the basis for controlling the charge. The steps of FIG. 5 are similar to those shown in FIG. 3. However, methodology 70 uses a hysteresis control methodology (e.g. bang-bang control) that switches the charging current for the battery between at least two different discrete non-zero charging currents based on a temperature of the IMD.

Methodology 70 includes two different discrete current controlled charge phases. High temperature current controlled charge phase 74 which charges the IMD's battery at a lower current of C/8 based on the temperature of the implant being above a temperature threshold. In contrast, when the temperature of the implant is below the temperature threshold, or below another temperature threshold, the battery may be charged at a higher current of C/4 as shown by low temperature current controlled charge phase 75.

For example, if a programmer wished to avoid going above a temperature of 40° C., and a 1° C. margin of error is used, the programmer could select a temperature threshold of 39° C. for initiating the high temperature current controlled charge phase 74. Additionally, the another temperature threshold of 38° C. could be chosen for initiating the low temperature current controlled charge phase 75. In this example, when the temperature of the IMD reaches 39° C. while charging at C/4, the current for charging the battery would be decreased to C/8, then when the temperature of the IMD reaches 38° C. the battery charge would be increased back to C/4. In one example embodiment, the temperature threshold may be selected to be equal to 37-42° C. and the other temperature threshold may be selected to be equal to 36-41° C.

Choice of set point and deadband may be varied based on historical data (e.g. long-term heat exposure). For patients exposed to more heat from charging (e.g. due to a higher power therapy or a deeper implant), the setpoint might be decreased. A patient with sensitive skin might be permitted to have a lower temperature set point.

A simple negative feedback control based on hysteresis can be implemented with a deadband region around the temperature setpoint (e.g. 40° C.) where no change in charging rate occurs might be defined by a temperature between the setpoint and an upper limit on the high side (e.g. +1° C. for 41° C.) and some temperature between the temperature setpoint and the default non-charging temperature (e.g. 38° C. if the default temperature was 37° C.). The IMD initiates the current controlled phase of charging at the faster recharge rate (e.g. C/4) during the low temperature current controlled charge phase 75 when below the upper deadband limit, and switches to charging at the slower rate (e.g. C/8) of the high temperature current controlled charge phase 74 when the temperature crosses from the deadband through the lower limit.

The IPG may be programmed with additional safety logic to prevent initiation of charging when temperature is above an upper temperature limit and may switch charging off in the event that the upper temperature limit is reached.

Figure 6:
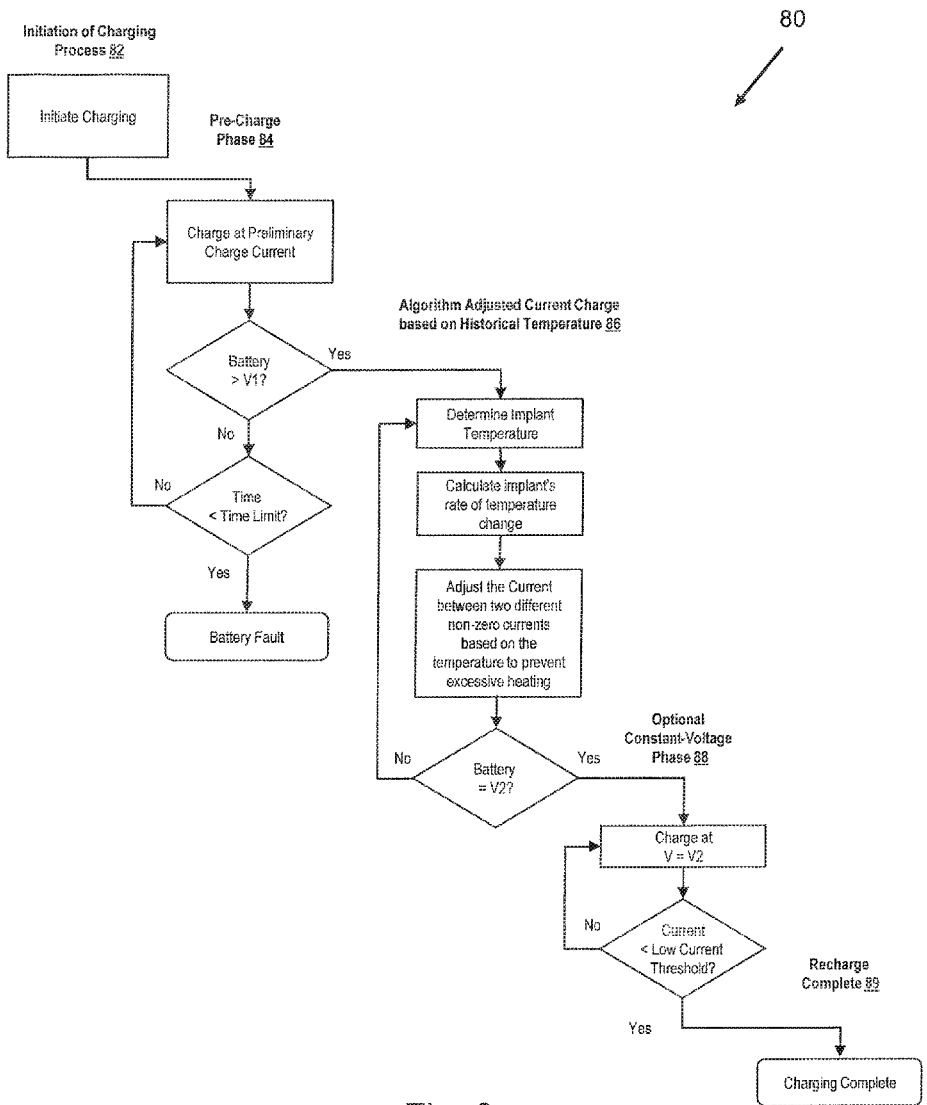
FIG. 6 is still another example flow chart of a current controlled charging methodology that is based on historical temperature information.

FIG. 6 is another example flow chart of a current controlled charging methodology 80, with an optional voltage controlled charging phase 88, that uses charging parameters that include both voltage and temperature as the basis for controlling the charge. The steps of FIG. 6 are similar to those shown in FIG. 3. However, methodology 80 uses an algorithm based current control that is based on historical temperature information 86 and/or present temperature information sensed by the temperature sensor of the IMD. The temperature sensor of the methodology 80 obtains the historical temperature information and present temperature information based on the temperature information sensed by the temperature sensor over a period of time. A charge controller is used for controlling a current of the battery charge signal, the current is determined using an algorithm that is based on temperature information and historical temperature information.

Figure 7:
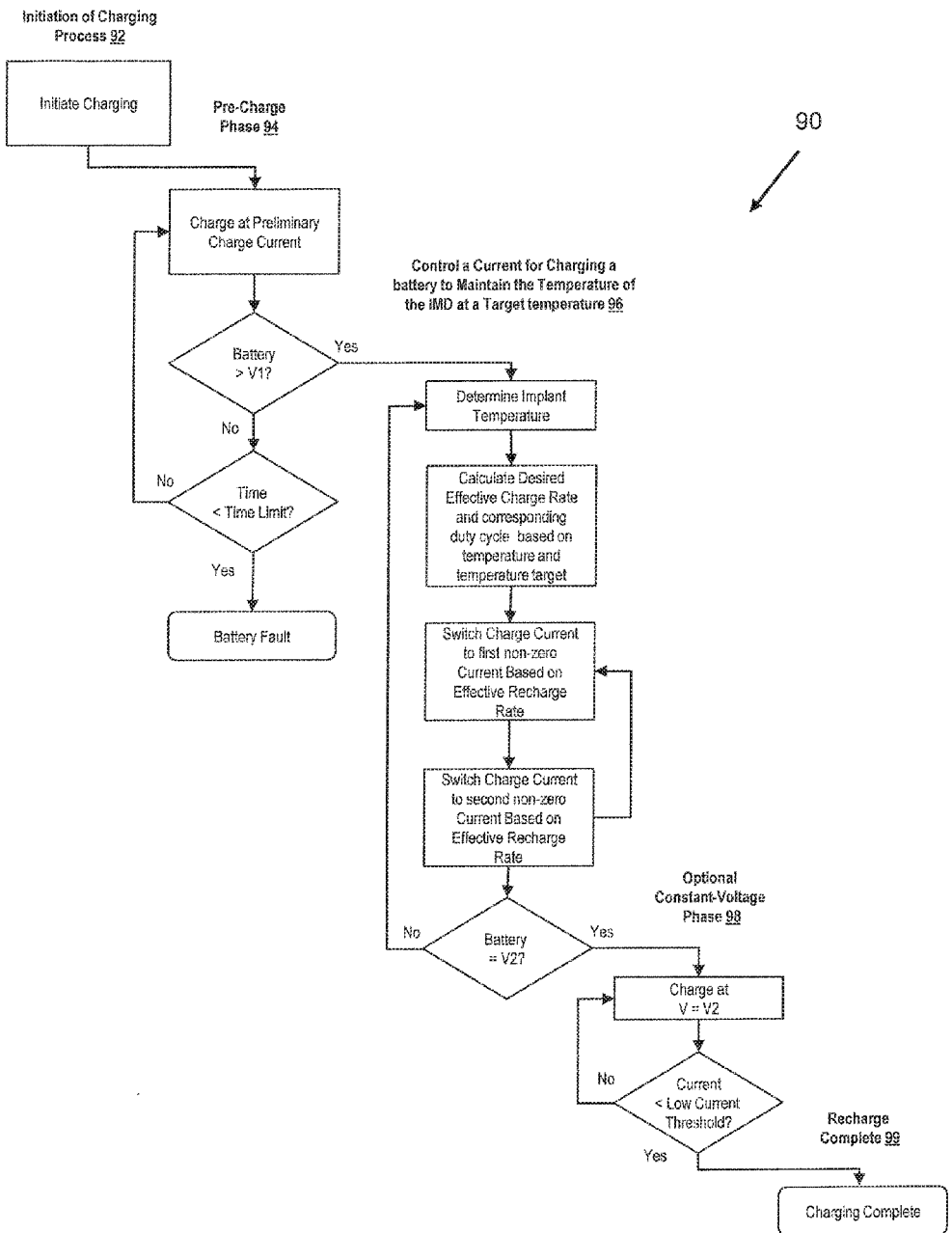
FIG. 7 is yet another example flow chart of a current controlled charging methodology that controls the current for charging a battery to maintain the temperature of the implantable medical device at a target temperature.

FIG. 7 is yet another example flow chart of a current controlled charging methodology 90, with optional voltage controlled charging phase 98, that uses charging parameters that include both voltage and temperature as the basis for controlling the charge. The steps of FIG. 6 are similar to those shown in FIG. 3. However, methodology 80 controls a current for charging a battery to maintain the temperature of the IMD at a target temperature 96. The temperature of the IMD is determined with a temperature sensor. A charge controller calculates an effective charge current for recharging the battery based on the temperature of the implant (e.g. present and/or historical temperature) and the target temperature. Optionally, the charge controller also controls continuous switching of the recharging rate (e.g. battery charge signal) between at least two different discrete non-zero currents (e.g. the first non-zero charge current and the second non-zero charge current) to obtain a temperature equal to the target temperature. For example, the current may be switched over a time interval. By varying the duty cycle of the two discrete charging rates an arbitrary charging rate can effectively be synthesized which allows the IMD to stay substantially at the target temperature within a few tenths of a degree. For example, if the effective charging rate was equal to C/6 is calculated as the current necessary to maintain target temperature, the charge controller of the IMD may provide a current of C/4 for 5 seconds and then switch to a charge rate of C/8 for 10 seconds and then repeat this cycle for the duration required, thus resulting in an effective charge current of C/6 and a cycle period of 15 seconds. By allowing an arbitrary effective charge current between two or more values, more sophisticated control methods than simple hysteresis (e.g. bang-bang control) may be used to recharge at an optimal constant-current charge rate.

Allowing an effective charge current, as described above, allows the use of linear negative feedback to calculate the desired effective recharge current and corresponding duty cycle based on implant temperature. Linear negative feedback methods suitable for calculating the effective charge current include simple proportional control or even a full proportional integral differential (PID) controller. Fuzzy logic and other predictive control methodologies may also be utilized.

The initial effective current, as controlled by duty cycle, might be chosen based on historical data (last used recharge rate) or based on the starting temperature (for example if the patient had a fever or was in a colder environment).

Another example method of establishing the initial target value for an effective charge current may be to perform a characterization period early in a charging cycle using hysteresis controlled charging as described above. The IPG charge controller monitors the amount of time spent at each discrete charging current and averages the temperature over that time period. Average temperature would then be compared to a target temperature (for example,) to define an error value. Then, a new target recharge rate is computed using the average charging current of the characterization period and the error.

Figure 8:
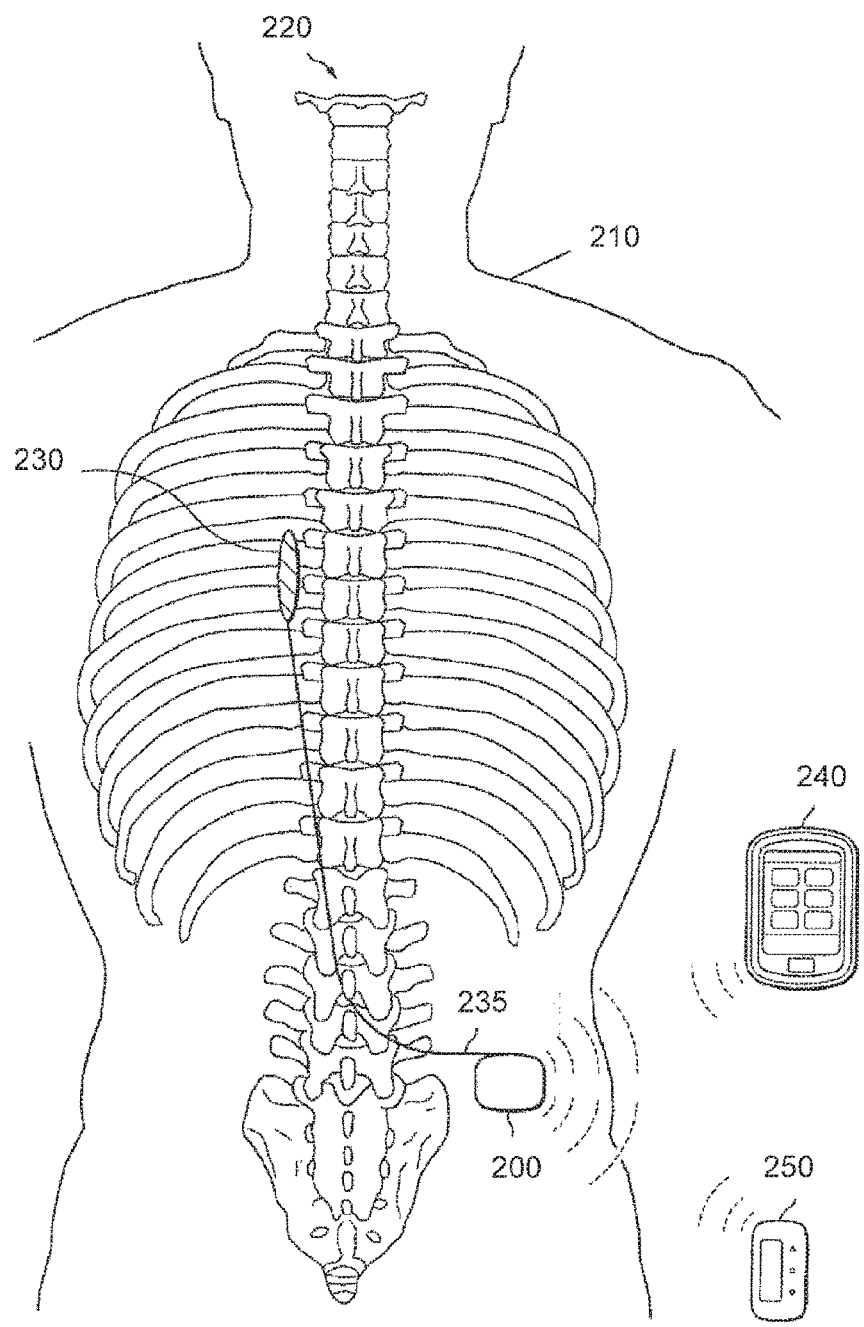
FIG. 8 shows an implant that is implanted in a patient.

FIG. 8 shows an example application of an implanted medical device 200 for providing spinal cord stimulation or neuro-stimulation to a patient 210. In FIG. 8, the implanted medical device is an implantable pulse generator (IPG) 200 shown implanted in a patient for providing stimulation to the patient's spinal cord (in the spine 220) for the purpose of providing pain therapy. The IPG 200 can be comprised of an internal battery (that may include a rechargeable battery), a controller, pulse generation electronics, protection/conditioning circuits, and a contact assembly for connecting to an electrode array. The IPG 200 can be supported by an external battery (such as for charging the battery of the internal battery), and a clinician programmer 967 and a user controller 968. Also shown is the human spine 210 in proximity with the stimulation Electrodes 230 that are attached to the IPG 200 via electrode leads 235. Optionally, the programmers and controllers may also be combined with an external charger to provide adjustment of IPG parameters and charging of the implant battery.

The leads and electrodes may be positioned anywhere along the spine to deliver the intended therapeutic effects of spinal cord electrical stimulation in the desired region of the spine. The distal end of the lead with its accompanying electrodes may be located in the epidural space and adjacent a desired portion of the spinal cord using well-established and known techniques for implanting and positioning SCS leads and electrodes, and the IPG 200 may be programmed using a clinician programmer 240 or other type of programmer 250 (such as a patient controller), as desired. Programmers may also include inductive chargers similar to the external charger 2 of FIG. 1. The electrode leads 965 can be connected to the IPG via a contact assembly as described in this application.

Although the example application of FIG. 8 depicts a neuro-stimulator, the IMD of FIG. 8 may also represent other stimulators for pain suppression, hearing aids (e.g. cochlear devices), cardiac pacemakers, and defibrillators. The IMD may also be used for drug infusion and dispensing systems, nerve and bone growth stimulators, digestive track stimulators, artificial vision apparatus, artificial organs including artificial hearts, bladder stimulators, and for the purposes of implanted sensors that monitor but do not actively stimulate tissue.

many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method for charging a battery in a medical device, the method comprising the steps of:

providing a temperature sensor in the medical device;
storing a plurality of temperature measurements obtained from the temperature sensor over a period of time;
analyzing said plurality of temperature measurements to determine historical temperature information; and
adjusting a charging rate of the battery based on the determined historical temperature information to optimize the charging of the battery, wherein the adjusting comprises transitioning the charging rate of the battery between a plurality of different non-zero constant current modes and at least one constant voltage mode.

2. The method of claim 1, wherein said historical temperature information includes a temperature trend determined by calculating a rate of change of the plurality of temperature measurements over time.

3. The method of claim 1, wherein said charging rate is adjusted by using a negative feedback control based on hysteresis determined from said historical temperature information.

4. The method of claim 1, wherein said charging rate is adjusted based on both said historical temperature information and current temperature information obtained from said temperature sensor.

5. The method of claim 1, wherein said charging rate is adjusted based on both said historical temperature information and a starting temperature determined at a time battery charging is starting.

6. The method of claim 1, wherein said battery is charged using a charging device configured for wirelessly charging said medical device.

7. The method of claim 6, wherein said medical device is implanted in a patient, and wherein said charging device is provided outside of the patient.

8. The method of claim 1, wherein said charging rate of the battery is controlled using the historical temperature information to optimize the charging of the battery within desired temperature constraints.

9. The method of claim 1, wherein the providing of the temperature sensor comprises providing a plurality of temperature sensors located at different locations of the medical device, and wherein the plurality of temperature measurements are obtained from the plurality of temperature sensors over the period of time.

10. A method for charging a battery in a medical device, the method comprising the steps of:

providing a battery charging device for charging the battery in the medical device;
providing a temperature sensor in the medical device;
transmitting a plurality of temperature measurements from the medical device to a battery charging device over time;
storing the plurality of temperature measurements in the battery charging device;
analyzing said plurality of temperature measurements to determine historical temperature information; and
adjusting a charging rate of the battery charging device for charging the battery based on the determined historical temperature information to optimize the charging of the battery within desired temperature constraints, wherein the adjusting comprises transitioning said charging rate of the battery between a plurality of different non-zero constant current modes and at least one constant voltage mode.

11. The method of claim 10, wherein said historical temperature information includes a temperature trend determined by calculating a rate of change of the plurality of temperature measurements over time.

12. The method of claim 10, wherein said charging rate is adjusted by using a negative feedback control based on hysteresis determined from said historical temperature information.

13. The method of claim 10, wherein said charging rate is adjusted based on both said historical temperature information and current temperature information obtained from said temperature sensor.

14. The method of claim 10, wherein said charging rate is adjusted based on both said historical temperature information and a starting temperature determined at a time battery charging is starting.

15. The method of claim 10, wherein said battery charging device is configured for wirelessly charging said medical device.

16. The method of claim 15, wherein said medical device is implanted in a patient, and wherein said battery charging device is provided outside of the patient.

17. The method of claim 10, wherein the providing of the temperature sensor comprises providing a plurality of temperature sensors located at different locations of the medical device, and wherein the plurality of temperature measurements are obtained from the plurality of temperature sensors over time.

18. A method for charging a battery in a medical device, the method comprising the steps of:
providing a receiver in the medical device which is implanted in a patient;
providing a temperature sensor in the medical device;
receiving, via the receiver, a wireless power signal from an external battery charging device;
converting the wireless power signal into a battery charge signal including power for recharging the battery;
transmitting a plurality of temperature measurements from the medical device to the battery charging device over time;
analyzing said plurality of temperature measurements to determine historical temperature information including a temperature trend determined by calculating a rate of change of the plurality of temperature measurements over time; and
changing a current of the battery charge signal based on the determined historical temperature information to optimize the charging of the battery within desired temperature constraints, wherein said battery charge signal is changed from a first non-zero current to a second non-zero current that is different from the first non-zero current, and wherein said changing of the current of the battery charge signal is based on the historical temperature information.

19. The method of claim 18, where said changing the current of the battery charge signal further comprises: decreasing the current when a current temperature sensed by said temperature sensor indicates an increased temperature in the medical device.

20. The method of claim 19, where said changing the current of the battery charge signal further comprises: increasing the current when a current temperature sensed by said temperature sensor indicates a decreased temperature in the medical device.

21. The method of claim 18, wherein said changing the current of the battery charge signal further comprises: controlling the current of the battery charge signal based on a temperature sensed by the temperature sensor, such that when the temperature is less than a low temperature threshold the battery charge signal is provided at a first non-zero current, and when the temperature is greater than a high temperature threshold the battery charge signal is provided at a second non-zero current that is less than the first non-zero current.

22. The method of claim 18, wherein said changing the current of the battery charge signal comprises: calculating an effective charge current of the battery charge signal based on a target temperature, a current temperature, and the historical temperature information to prevent the current temperature from exceeding a temperature threshold while maintaining a high battery charge rate.

23. The method of claim 22, wherein said changing the current of the battery charge signal further comprises: switching the current of the battery charge signal between at least two different discrete non-zero currents during a time interval based on the targeted temperature, such that a time weighted average of the at least two different discrete non-zero currents during the time interval is equal to the effective charge current.

24. The method of claim 18, wherein a charging rate of the battery is transitioned between a plurality of different non-zero constant current modes and at least one constant voltage mode.

25. The method of claim 18, wherein the providing of the temperature sensor comprises implementing a plurality of temperature sensors at different locations of the medical device, and wherein the plurality of temperature measurements are measured by the plurality of temperature sensors over time.

* * * * *